United States Patent [19]

Miura et al.

[11] Patent Number: 5,308,774
[45] Date of Patent: May 3, 1994

[54] LIQUID CHROMATOGRAPHIC METHOD AND APPARATUS FOR ANALYZING BIOLOGICAL SAMPLES

[75] Inventors: Junkichi Miura; Masahito Ito; Yoshio Fujii; Hiroshi Satake, all of Katsuta; Kasumi Yoshida, Mito, all of Japan

[73] Assignee: Hitachi, Ltd., Tokyo, Japan

[21] Appl. No.: 625,823

[22] Filed: Dec. 11, 1990

[30] Foreign Application Priority Data

Jan. 8, 1990 [JP] Japan .................................. 2-510

[51] Int. Cl.$^5$ ...................... G01N 30/14; G01N 33/88
[52] U.S. Cl. .................................. 436/87; 436/63; 436/111; 436/161; 436/172; 436/175; 436/179
[58] Field of Search ............... 436/63, 87, 111, 112, 436/161, 172, 175, 177, 178, 179

[56] References Cited

U.S. PATENT DOCUMENTS

| | | | |
|---|---|---|---|
| 3,934,979 | 1/1976 | McClure | 23/230 B |
| 4,705,757 | 11/1987 | Ohkura | 436/172 |
| 5,011,608 | 4/1991 | Damjanovic | 210/656 |

FOREIGN PATENT DOCUMENTS

| | | |
|---|---|---|
| 58-108457 | 6/1983 | Japan . |
| 6188148 | 10/1984 | Japan . |
| 6192599 | 10/1984 | Japan . |
| 60-143766 | 7/1985 | Japan . |

OTHER PUBLICATIONS

"A New HPLC Concept for Directly Analyzing Drugs in Biological Matrices: Shielded Hydrophobic Phases", pp. 2–4, Sep. 1988, 17th International Symposium on Chromatography.

*High Performance Liquid Chromatography Handbook,* Analytical Chemical Society of Japan, Maruzen Corp., Nov. 1985.

*Primary Examiner*—James C. Housel
*Assistant Examiner*—David Redding
*Attorney, Agent, or Firm*—Antonelli, Terry, Stout & Kraus

[57] ABSTRACT

Physiologically active substances contained in a biological sample not subjected to deproteinization can be converted to their derivatives at a high efficiency without being adversely affected by the protein present in the sample, and accordingly the analysis of said physiologically active substances in the form of said derivatives can be performed at a high precision.

37 Claims, 9 Drawing Sheets

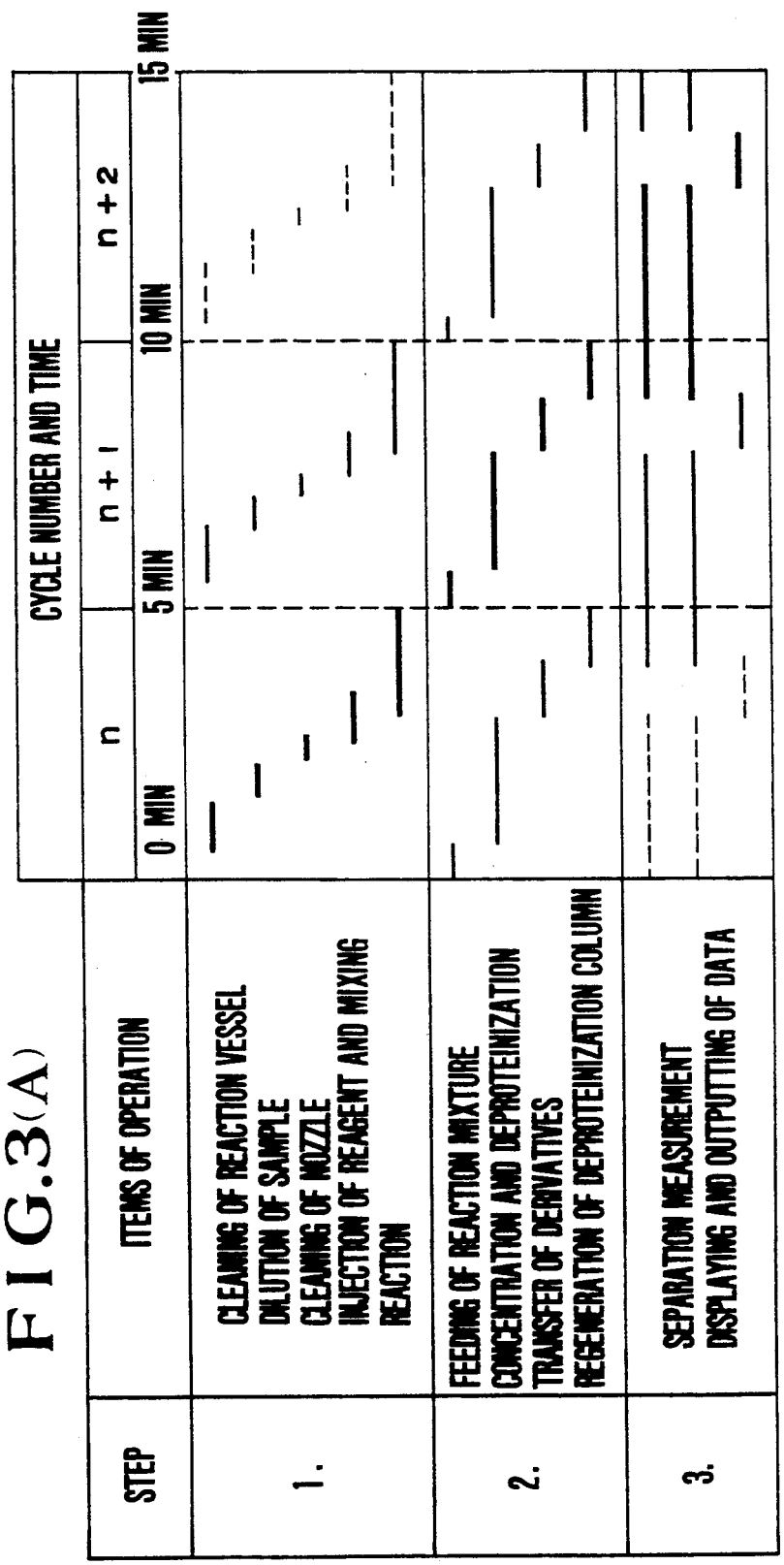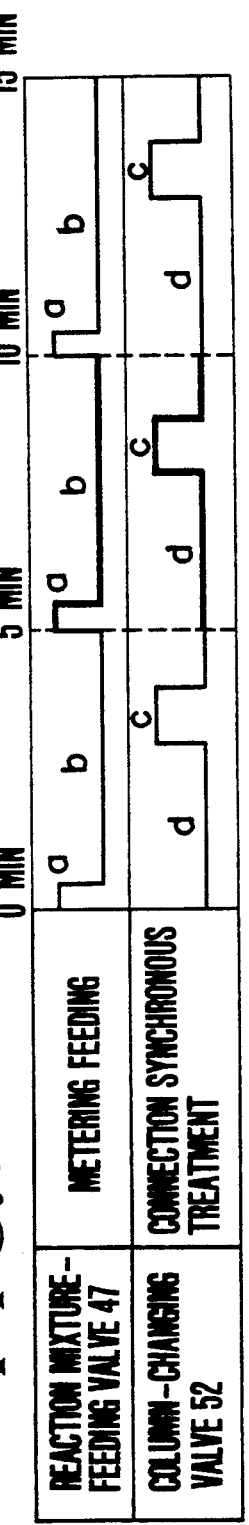
FIG.3(A)
FIG.3(B)

LIQUID CHROMATOGRAPHIC METHOD AND APPARATUS FOR ANALYZING BIOLOGICAL SAMPLES

The present invention relates to a chromatographic method and a liquid chromatographic analyzer for analyzing a biological sample and particularly to an analytical method and an analyzer suited for prelabeling the physiologically active substances contained in a blood or cerebrospinal fluid (hereinafter CSF), to measure the individual components of the physiologically active substances qualitatively and quantitatively.

Physiologically active substances (e.g. hormones) contained in body fluids (e.g. blood, CSF) are very small in content but have a large effect on the physiology of a living body. Therefore, it is in wide practice to analyze and inspect the individual components of the physiologically active substances to utilize the results in pathological studies or researches.

Of the physiologically active substances, local hormones such as catecholamines, prostaglandin and the like are present in, for example, blood only in an amount of picogram ($10^{-12}$ g/ml) order. Therefore, the analysis of these physiologically active substances is readily affected by other components also present in the sample in an overwhelmingly large amount. In order to avoid it, the analysis of the physiologically active substances is made by separating them into individual components by liquid chromatography, or by reacting the physiologically active substances with a fluorescent labeling agent and measuring the labeled substances by a fluorophotometer.

As the prior art for labeling (converting to derivatives) catecholamines by a prelabeling method and subjecting the labeled catecholamines to chromatography, there are known the methods disclosed in JP-A-61-88148 and 60-143766.

According to the method of JP-A-61-88148, alumina is added to a test sample to allow the catecholamines in the sample to be adsorbed on the alumina while reacting dansyl chloride therewith in the course of adsorption to convert the catecholamines to the derivatives. Then, the derivatives are desorbed from the alumina and the solution containing the derivatives is concentrated by evaporation. The concentrate thus prepared is injected into the flow path of a liquid chromatograph to separate the concentrate into the individual components of the catecholamine derivatives and the fluorescence of each individual component is detected.

According to the method of JP-A-60-143766, a biological sample such as plasma, urine or the like is injected into a flow path and then three types of reaction reagents are introduced successively into said flow path and during their passage through a reaction coil, the catecholamines in the sample are labeled (converted to their derivatives). The labeled catecholamines thus prepared are captured and concentrated by a concentrating column and then transferred into a separating column to separate the labeled catecholamines into individual components and the fluorescence of each individual component is detected.

As the prior art for labeling prostaglandin by a prelabeling method and subjecting the labeled prostaglandin to chromatography, there are known the methods disclosed in JP-A-61-92599 and 58-108457.

The method of JP-A-61-92599 suggests a method for analyzing prostaglandin by high performance liquid chromatography, wherein a sample is labeled to convert the physiologically active substances in the sample to fluorescent substances and then the fluorescent substances are separated into individual components to measure them by a fluorescence detector. However, the document gives no further details.

In the method of JP-A-58-108457, a biological sample is subjected to reversed phase (distribution) chromatography to obtain a solution containing prostaglandin, the solution is concentrated, and the concentrate is diluted and then reacted with a fluorescent labeling agent capable of reacting with the carboxyl group of prostaglandin, to convert prostaglandin to its ester form. The thus prepared ester form is poured into the flow path of a liquid chromatograph to separate into individual components, and each component is measured by a fluorescence detector.

In the prior art JP-A-61-92599, only a possibility of sample prelabeling is suggested and no specific method for prostaglandin analysis is disclosed which can be effectively carried out by those skilled in the art. In the methods of JP-A-61-88148 and JP-A-58-108457, a fairly long time is required for the preparation of a test solution to be fed into the flow path of a liquid chromatograph and, moreover, the automation of the overall analytical procedure is difficult; therefore, the methods are unfit for routine works such as clihical examinations.

When the utility is focused on, a method such as disclosed in JP-A-60-143766 is advantageous because in the method the physiologically active substances in a sample are prelabeled, then the prelabeled substances are separated into individual components, and each component is measured by fluorophotometry.

The present inventors tried to analyze physiologically active substances in blood and CSF samples, using a chromatography employing a prelabeling method; however, no sufficient measurement precision was obtained. This low analytical precision is caused by the proteins present in the sample used. Accordingly, in order to achieve a high-precision analysis for the physiologically active substances contained in a biological sample, it is necessary to apply a pretreatment of deproteinization to the sample. However, the pretreatment of the sample by precipitation and separation, ultrafiltration or the like requires an operation of few to several stages, making the overall analytical procedure complex. Further, the long time taken by the deproteinization treatment invites the decomposition and/or loss of components to be analyzed, during the operation.

An object of the present invention is to provide a method for analyzing a biological sample wherein the physiologically active substances to be measured, contained in the sample can be efficiently converted to their derivatives in a state that the sample contains proteins, as well as to an analyzer using said method.

Another object of the present invention is to provide a method for analyzing a biological sample wherein the physiologically active substances to be measured, contained in the sample are decomposed or lost in a minimal amount during the analytical operation, as well as to an analyzer using said method.

Still another object of the present invention is to provide a method for analyzing a biological sample wherein the physiologically active substances to be measured, contained in the sample can be converted to their derivatives and the derivatives can be separated into individual components, both in simple procedures, as well as to an analyzer using said method.

In the present invention, a blood or CSF sample not subjected to deproteinization, a reagent and a diluent are fed into a reaction vessel, whereby the physiologically active substances to be measured, contained in the sample are reacted with the reagent and converted to their derivatives. This reaction for converting the physiologically active substances to their derivatives is allowed to proceed to the completion in the reaction vessel, or is successively conducted in a predetermined portion of a flow path provided after the reaction vessel.

The reaction mixture is then transferred to a separating column to separate said derivatives into individual components, and each component is detected by an optical detector. The reaction mixture is subjected or not subjected to a deproteinization treatment before being transferred to the separating column. When the deproteinization treatment is carried out, the reaction mixture is fed into a deproteinizing column, wherein the derivatives of physiologically active substances are adsorbed in the deproteinizing column and concurrently the proteins contained in the sample are discharged from the deproteinizing column. When the deprotenization treatment is not carried out, there is used a separating column packed with a packing on which the proteins cause substantially no damage.

Prior to the above reaction for converting the physiologically active substances to their derivatives, the biological sample containing the physiologically active substances is diluted 8- to 20-fold by the diluent, whereby the concentration of proteins in the diluted sample (the mixture) becomes 1% or less. The reaction for converting the physiologically active substances to their derivatives is carried out at 30-60° C.

BRIEF DESCRIPTION OF DRAWINGS

FIG. 3A and FIG. 3B are diagrams showing the operation time schedule of each section or unit in the analyzer of FIG. 1;

Figure 1:
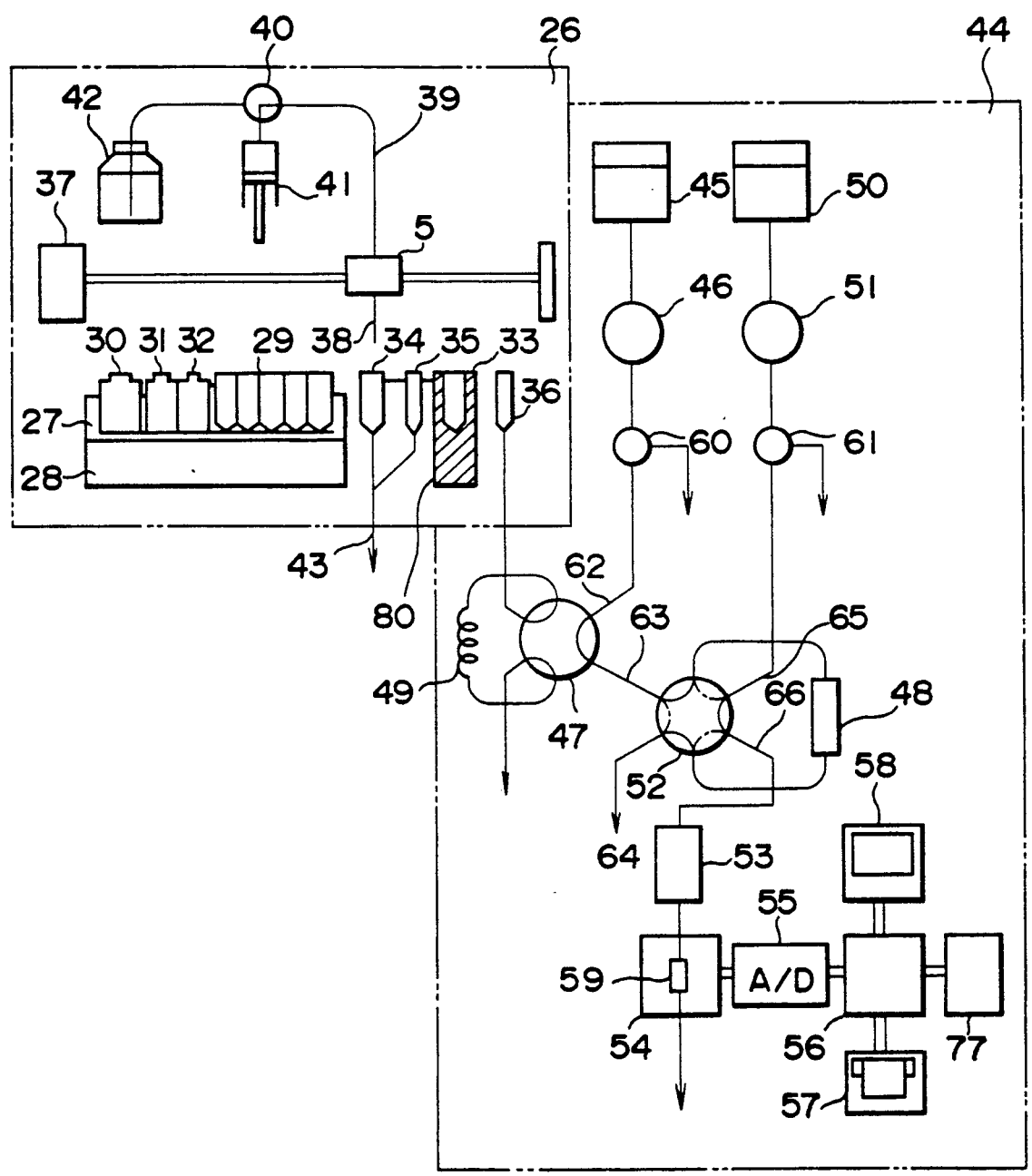
FIG. 1 is a schematic view showing the constitution of one embodiment of the analyzer of the present invention.

The following numerals used in the above drawings refer to the following sections, units or parts of the analyzers.

26: autosampler, 29: sample vessel, 30: reagent vessel, 33: reaction vessel, 36: injection port, 38: injection nozzle, 42: diluent tank, 47: mixture-feeding valve, 48: deproteinizing column, 49: metering tube, 52: flow path-changing valve, 53 and 100: separating column, 54: fluorophotometer, 56: control unit, 82: mixing vessel.

In a biological sample such as blood or CSF, containing proteins in an amount of 5-10%, the addition of a reagent to the sample hardly gives rise to the conversion of the physiologically active substances (e.g. catecholamines, prostaglandin) contained in the sample to their derivatives, when the sample has not been subjected to a pretreatment of deproteinization. The experiments conducted by the present inventors showed that this phenomenon is due to the presence of proteins in a high concentration which causes the adsorption of the reagent and reaction accelerator by the protein components.

The present inventors further found that when the protein concentration in the mixture containing the reagent and the biological sample is 1% or less, the influence of the proteins on the reaction for converting the physiologically active substances to their derivatives is negligibly small, and the reaction can be carried out very efficiently.

Based on these findings, in the present invention, a blood or CSF sample is diluted appropriately, preferably 8- to 20-fold by a diluent, prior to the reaction for converting the physiologically active substances contained in the sample to their derivatives. The degree of dilution by the diluent is set at a desired level depending upon the type of the sample or the type of the reagent used. The setting of the dilution degree at a specific value enables the automation of analyzer which is useful in treating a large number of similar samples as in clinical examinations.

The dilution degree of a biological sample is preferably 20-fold or less. It is because too high a dilution degree makes it difficult to attain the high-precision measurement, i.e. the high-sensitivity detection, of the physiologically active substances contained in the sample in a very small amount, and because such a dilution degree makes too large the total volume of the solution to be treated.

The reaction for converting the physiologically active substances (e.g. catecholamines, prostaglandin) to their derivatives is carried out preferably under a heated state of 30-60° C. The temperature of 30° C. or higher is preferable because such a reaction temperature higher than room temperature is easy to control and can accelerate said reaction. The temperature of 60° C. or lower is preferable because it can prevent the proteins in the sample from being denatured in a relatively short time at high temperatures. The denaturation of the proteins undesirably invites their precipitation together with other components, which makes the measured values of the components to be measured, smaller than the actual values. For information, there was observed no protein denaturation until 3 minutes even when the sample was heated at 60° C.

The separation of catecholamines into individual components by chromatography enables the detection of such components as epinephrine, norepinephrine, dopamine and the like. The separation of prostaglandin into individual components by chromatography enables the detection of such components as thromboxane $B_2$, prostaglandin $E_2$, 6-ketoprostaglandin $F_{1\alpha}$, prostaglandin $E_1$ and the like. By converting these physiologically active substances into their derivatives and subjecting the derivatives to fluorometric analysis, absorptiometric analysis or conductometric analysis, each component of the physiologically active substances contained in biological samples in a very small amount can be detected at a high sensitivity.

The physiologically active substances, when converted to their derivatives, each have a larger molecular weight than before the conversion, and accordingly have a higher chemical stability and are adsorbed more easily by the packing packed in the separation column. This increase in adsorbability is particularly effective when a deproteinizing column is provided before the separating column to separate the proteins from the derivatives of the physiologically active substances. By continuously feeding the reaction mixture containing the derivatives and the proteins into the deproteinizing column in such a way that the reaction mixture is sandwiched by a transferring solution, the derivatives are adsorbed in the deproteinizing column while the proteins are discharged from the column right after being fed into the column. The packing packed in the deproteinizing column is preferably an internally reversed phase type packing or an ion exchange group-containing polymer type packing. The deproteinizing column has a function of separating the proteins from the derivatives of the physiologically active substances, as well as a function of concentrating the diluted derivatives.

When there is used a separating column packed with a packing of a type not adsorbing the proteins, no deproteinizing column is necessary before the separating column. As such a packing, there can be used the same packing as used in the deproteinizing column. In this case, there can be obtained the above-mentioned merit by the larger molecular weight of physiologically active substances when converted to their derivatives. That is, the proteins present in the reaction mixture together with the derivatives of physiologically active substances are discharged from the separating column right after being fed thereinto, whereby the separability of proteins from derivatives is enhanced.

In a preferred embodiment of the present invention, an autosampler is used for preparing a sample solution to be injected into an analytical section. This autosampler comprises a diluent feeder equipped with a movable nozzle. The movable nozzle can move to the positions of a sample vessel, a reagent vessel, a standard solution vessel, a mixing vessel, a nozzle-cleaning port, a mixed solution-injecting port, etc. The nozzle has various functions such as sample injection into mixing vessel, reagent injection into mixing vessel, diluent injection into mixing vessel, transfer of mixed solution from mixing vessel to separating and analytical section, and the like and is controlled so as to perform said functions.

The embodiment of the present invention is constituted so as to carry out the reaction for converting the physiologically active substances in a biological sample to their derivatives, prior to deproteinization. When the reaction is carried out using, for example, 1,2-diphenylethylenediamine (DPE) which is a reagent for converting catecholamines to their derivatives, the catecholamines are converted to molecules having four cyclic fragments, as compared with the catecholamine molecules having one cyclic fragment. Accordingly, the catecholamine derivatives have higher hydrophobicity and can be easily separated from the proteins in said sample, in a small precolumn.

As the fluorescent labeling agent used as the reagent for converting catecholamines to their derivatives, there can be used, for example, 1,2-diphenylethylenediamine (DPE). The fluorescent labeling agent is prepared as a solution containing 60 mM of DPE, 2 mM of potassium ferricyanide, 40% of acetonitrile, etc. As the eluting solution fed into the separating column to separate the catecholamine derivatives into individual components, there is used, for example, a solution containing acetonitrile, methanol and an aqueous solution of 50 mM of lithium nitrate and 10 mM of sodium dodecyl sulfate, at a ratio of 5:2:4.

As the fluorescent labeling agent used as the reagent for converting prostaglandin to its derivatives, there can be used monodansylcadaverine (MDC). The fluorescent labeling agent is prepared as a solution containing 6 mM of MDC, 86 mM of diethyl phosphorocyanitate (DEPC), etc. As the eluting solution used to separate the progtaglandin derivatives, there can be used a solution consisting of water, tetrahydrofuran and acetonitrile. The excitation wavelength and fluorescent wavelength of the fluorescence detector used are preferably 340 nm and 520 nm, respectively.

Below are shown the embodiments of the present invention using a single separating column. The use of a single separating column makes the analytical mechanism simple as compared with the case using a plurality of separating columns. The biological samples to which the present invention can be preferably applied are plasma, serum, CSF, etc.

Embodiments of the automatic catecholamine analyzer utilizing the present invention are described referring to the accompanying drawings.

FIG. 1 is a schematic view showing the overall constitution of an automatic catecholamine analyzer utilizing the present invention. This analyzer comprises a sample-feeding section 26 accommodating various vessels and an injection mechanism, and a concentrating and separating section 44 for carrying out concentrating and separating operation in a flow path system. Hereinafter, the sample-feeding section 26 is referred to as "autosampler" and the concentrating and separating section 44 is referred to as "analytical section".

The autosampler 26 has a non-movable portion or a reaction portion 90 and a detachable sample rack 27. Said sample rack 27 is set on a sample stage 28 and holds a plurality of sample vessels each containing a plasma sample. In said sample rack 27 are also provided a reagent (fluorescent labeling agent) vessel 30, an internal standard solution vessel 31 and a standard sample vessel 32. In the autosampler 26, there are provided a reaction vessel 33, a nozzle-cleaning tank 34, a drain port 35 and an injection port 36, at the fixed positions close to the sample stage 28.

An injection nozzle 38 has the functions of injecting the sample and reagent into the reaction vessel 33 by pippeting and of transferring the resulting reaction mixture to the injection port 36. A driving mechanism 37 has a function to move the nozzle 38 along the X-, Y- and Z-axes which cross vertically each other. The mechanism can move the nozzle 38 freely in three dimensions (laterally and vertically) so that the nozzle can be positioned at any vessel or port on said autosampler. The upper end of said nozzle 38 is connected to an injection pump 41 and a diluent (also cleaning solution) tank 42 through a thin tube 39 (e.g. plastic tube) and a three-way valve 40. As the injection pump 41, there is used a syringe pump driven by a pulse motor. A thermostatic block 80 is provided for maintaining the temperature of the reaction vessel 33 at a predetermined level. In the sample stage 28 is incorporated a cooling means which keeps the sample and reagent on the sample rack 27 at a low temperature during the analysis.

The analytical section 44 consists of a precolumn flow path system in which the substances to be measured are concentrated and the unnecessary substances are removed, a separating column flow path system in which the substances to be measured are separated into individual components, and a measuring and operating portion. In the precolumn flow path system, a transferring and cleaning solution in its storage tank 45 is transferred at a constant rate by a pump 46 and sent into a deproteinizing column 48 through a valve 47. Also connected to said valve 47 is a metering tube 49 by which the flow of the reaction mixture injected from the injection port 36 is regulated so that a predetermined amount of the reaction mixture can be introduced into the analytical section.

In the separating column flow path system, an eluting solution in its storage tank 50 is transferred at a constant rate by a pump 51 and sent into a single separating column 53 through a column-changing valve 52. This column-changing valve 52 may be turned so that the eluting solution passes through the deproteinizing column 48 to transfer the derivatives of physiologically active substances adsorbed in the deproteinizing column 48 to the separating column 53. The measuring and operating portion comprises a fluorophotometer 54 for measuring the intensity of fluorescence of the substances eluted from the separating column 53, an A/D converter 55 which performs the operation and display of the measurement results, a control unit 56, a printer 57, a CRT 58, etc. Said fluorophotometer 54 has a flow cell 59. Changing valves 60 and 61 are provided to enable purging of the solutions in the pumps 46 and 51, respectively, when such is necessary.

As the diluent injected into the mixing vessel or reaction vessel 33 in carrying out the reaction for converting the physiologically active substances contained in a biological sample, to their derivatives, there is used such a diluent as to give no adverse effect on said reaction and cause no denaturation of the proteins contained in the sample. The diluent stored in the tank 42 and injected from the nozzle 38 is selected from water, an aqueous neutral salt solution (e.g. an aqueous solution containing about 0.1 M of sodium chloride), a buffer solution (pH: about 7) containing about 0.1 M of a phosphate, and so forth. The order of adding the sample and the reagent to the vessel 33 need not be as mentioned in this embodiment and may be changed as necessary depending upon the constitution of the analyzer of the present invention. The order can be any as long as the reaction for converting the physiologically active substances to their derivatives is carried out in a state wherein the sample has been diluted.

The transferring solution stored in the tank 45 is used to push out the reaction mixture in the metering tube 49 and transfer it to the deproteinizing column 48. As this transferring solution, there is used an aqueous solution containing about 0.1 M of sodium chloride. In the deproteinizing column 48, the transferring solution, together with the packing packed in said column, increases the adsorbability of the derivatives of physiologically active substances and facilitates the discharging of proteins.

When the deproteinizing column 48 is used as in the embodiment of FIG. 1, the packing packed in the separating column 53 is preferably, for example, a straight alkyl group-containing silica type packing or a reversed phase type packing (e.g. polymer gel type packing such as styrene, divinylbenzene, polyvinyl alcohol, methacrylate and the like). In this case, as the eluting solution fed into the separating column 53, there is used a solution containing acetonitrile ($CH_3CN$), methanol ($CH_3OH$) and water. The eluting solution stored in the tank 50 is used also to desorb the derivatives of physiologically active substances adsorbed in the deproteinizing column.

The analytical operation in using the analyzer of FIG. 1 is conducted in the order of (a) the conversion of the physiologically active substances in a biological sample to their derivatives on the autosampler, (b) the removal of the proteins present in the sample and the concentration of said derivatives, in the deproteinizing column, and (c) the separation of the derivatives into individual components in the separating column and the measurement of each component.

The analytical procedure in using the chromatographic catecholamine analyzer of FIG. 1 is described with reference to the flow chart of FIG. 2.

Cleaning of Reaction Vessel

After the start of the analytical operation in step 101, the reaction vessel 33 is cleaned in step 102. In this step, the nozzle 38 is moved to the position of the reaction vessel 33 and the pump 41 is actuated to inject the cleaning solution from its storage tank 42 into the reaction vessel. The cleaning solution is injected in an amount greater than the capacity of reaction vessel 33, with the excessive cleaning solution being discharged into the discharge pipe 43 through the drain port 35. Then, the nozzle 38 is lowered down to the bottom of the reaction vessel 33 to suck up the used cleaning solution in the vessel and then moved to the position of the drain port 35 to discharge the sucked-up solution therethrough. Prior to this operation (sucking-up of the used cleaning solution), it is necessary to suck up and keep a small amount of air in the front end of the nozzle 38 so that the used dirty solution sucked up by said nozzle does not diffuse into the fresh cleaning solution in the nozzle. (The operation of sucking up air to form a boundary before the sucking-up of the used cleaning solution is necessary also when sucking up the sample and the reagent in the later steps, but no description is made on this operation in the later steps to avoid complication of the description.) The above-described series of operations are repeated a plurality of times (for example, three times) to complete the cleaning of the reaction vessel 33.

Injection and Dilution of Sample

The sample (blood) is injected into the reaction vessel 33 and diluted in step 103. The nozzle 38 is first moved to the position of the internal standard solution vessel 31, lowered down thereinto to suck up a predetermined amount of the solution, raised up from said vessel 31, then moved to the position of the sample vessel 29 to suck up a predetermined amount of the sample to be analyzed, and then further moved to the position of the reaction vessel 33, and there the sample and internal standard solution held in the nozzle are injected into said reaction vessel 33. The internal standard solution is a standard solution used for correcting, for example, the variation of percent recovery from the column.

The addition of the internal standard solution is not always necessary. Thereafter, the three-way valve 40 is turned to suck the diluent in its tank 42 into the injection pump 41 in a predetermined amount. The three-way valve 40 is turned again and the syringe of the injection pump 41 is pushed into the inner portion of the pump cylinder to discharge the diluent of 10 times the volume of the sample taken in the reaction vessel 33, from the front end of the nozzle 38 into the reaction vessel 33. The actions of the injection pump 41 and the driving mechanism 37 are controlled by the control unit 56. In this embodiment, the amount of the sample taken is 0.1 ml and the amount of the diluent added is 1.0 ml. The sample is diluted by the addition of the diluent, in the reaction vessel 33.

Cleaning of Nozzle

The nozzle 38 is cleaned in step 104. The nozzle 38 is moved to the position of the drain port 35 and the cleaning solution is discharged from the nozzle to clean out contamination on the inner wall of the nozzle 38 due to the internal standard solution and the sample. Then, the nozzle is further moved to the position of the nozzle cleaning tank 34 and lowered down thereinto and the cleaning solution is discharged to clean the outside of the front end of the nozzle 38.

Injection of Reagent and Mixing

The reagent is injected into the reaction vessel 33 in step 105. The nozzle 38 is moved to the position of the reagent vessel 30 and a predetermined amount of the reagent for converting the physiologically active substances contained in the sample to their derivatives is sucked up into the nozzle. The sucked-up reagent is then injected into the reaction vessel 33 and mixed with the sample and internal standard solution previously injected into said reaction vessel. Mixing can be alternatively effected by the other methods, for example, a method comprising sucking up air into the nozzle, inserting the nozzle into the reaction vessel and discharging the air in the nozzle into the vessel, or a method comprising shaking or vibrating the reaction vessel by an external mechanical force or an electrical means. If the reagent is readily miscible with the sample and internal standard solution and discharged in a relatively large amount, mixing may be sufficiently made by merely discharging the reagent at a high speed.

Reaction

In step 106, a labeling reaction by fluorescent substance (reagent) is initiated to convert the catecholamines contained in the sample to the fluorescent derivatives. The mixed solution of the sample, the reagent and the diluent in the reaction vessel 33 is left in the reaction vessel 33 kept at a given temperature, for a predetermined period of time to allow the reaction to proceed, thereby effecting labeling by the fluorescent reagent.

Introduction of Reaction Mixture into Metering Tube

The reaction mixture in the reaction vessel 33 is introduced into the metering tube 49 in step 107. The reaction mixture in the reaction vessel 33, containing catecholamines which have substantially undergone the labeling reaction and turned into the derivatives, is sucked up into the nozzle 38. The nozzle is then moved to the position of the injection port 36 and inserted thereinto, and the reaction solution is inserted into the metering tube 49 by setting the reaction mixture-feeding valve 47 in the state shown in FIG. 1. When the valve 47 is turned after the metering tube 49 has been filled with the reaction mixture, the metering tube 49 connected to the port of the changing valve 47 is connected between the flow path 62 and the flow path 63 and a predetermined amount of the reaction mixture is transferred to the column 48 by the flow of the transferring solution.

Concentration and Deproteinization

In step 108, there are performed the capture of catecholamine derivatives in the deproteinizing column 48 and the removal of proteins and excess reagent. Concurrently, the concentration of catecholamine derivatives is conducted. As the reaction mixture is introduced into the deproteinizing column 48 by the flow of the transferring and cleaning solution, the catecholamine derivatives are captured by adsorption and accumulated in the deproteinizing column 48. The impurities which are to disturb the measurement to be made later, such as proteins and excess reagent, are passed through the deproteinizing column and discharged from the discharge port 64.

Transfer of Derivatives

In step 109, the catecholamine derivatives separated from impurities and captured in the deproteinizing column 48 are desorbed therefrom and introduced into the separating column 53. When the column-changing valve 52 is turned from the state shown by solid lines in FIG. 1 to the state shown by broken lines, the deproteinizing column 48 is connected between the flow paths 65 and 66, allowing the eluting solution to flow through the deproteinizing column 48, whereby the catecholamine derivatives in the deproteinizing column 48 are desorbed and transferred to the separating column 53 to separate the derivatives into individual components. When the column-changing valve 52 is again turned (to the solid-line state in the drawing) at the timing when the whole derivatives have been moved into the flow path 66, the eluting solution is allowed to flow directly into the separating column 53 without passing through the deproteinizing column 48, and the transferring and cleaning solution begins to flow into the deproteinizing column 48.

Separation

In step 110, the eluting solution is kept flowing into the separating column 53, whereby the catecholamine derivatives are separated into their components and norepinephrine (NE), epinephrine (E) and dopamine (DA) are eluted in and discharged from the separating column in the form of respective bands.

Regeneration of Deproteinizing Column

In step 111, the transferring and cleaning solution is flown into the deproteinizing column 48, synchronously with the separation of catecholamine derivatives into individual components in step 110, and the deproteinizing column 48 is regenerated into a state ready for receiving the next supply of reaction mixture.

Measurement

In step 112, the eluates from the separating column 53 are measured by the fluorophotometer 54. The derivative components separated and eluted in and discharged from the separating column 53 flow successively into the flow cell 59 in the fluorophotometer 54, and the intensity of fluorescence of each separated component is detected and subjected to operation to determine the concentration of each component.

Displaying and Outputting of Data

In step 113, the data obtained in step 112 are displayed and output by using the printer 57, the CRT 58, etc. In step 114, it is examined whether all the samples on the autosampler 26 have been subjected to the schemed treatment. If there still remains any untreated sample, the analytical operation is returned to step 102 to initiate a fresh analysis. When it is confirmed that all the samples have been treated, the operation proceeds to step 115 to complete the analysis using the analyzer of FIG. 1.

The analytical procedure when one sample is analyzed according to the present invention has been described above. In the following, there will be described the analytical procedure when a plurality of samples are continuously analyzed. FIGS. 3A and 3B show an example of the operational program of continuous analysis.

Figure 2:
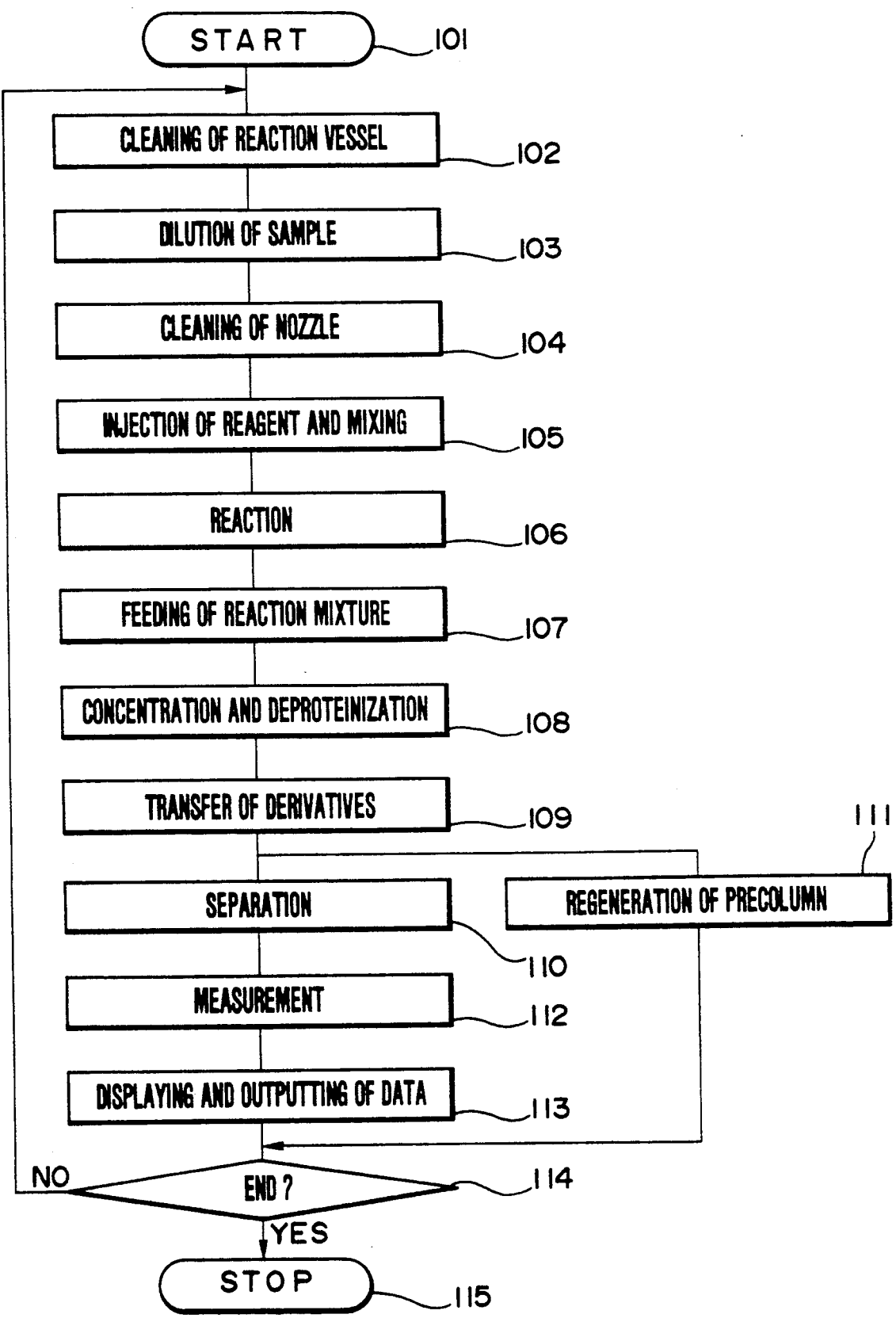
FIG. 2 is an illustration showing the flow of the analytical procedure in the analyzer of FIG. 1.

On the vertical axis of FIG. 3A, there are shown the operation items shown in the flow chart of analysis of FIG. 2, by dividing them in steps 1, 2 and 3. The first step principally comprises the operations for converting catecholamines into the derivatives on the autosampler. The second step comprises the operations for concentrating the catecholamine derivatives and removing proteins in the deproteinizing column. The third step comprises the operations for separating the catecholamine derivatives into individual derivatives in the separating column and measuring each component. Each step is formed so that the time allocation for each step is suited for the overall operational program. On the horizontal axis, there are shown the number of cycles and elapsed time in the on-going analytical program. The program is formulated so that all the operation items of the first to third steps are completed in one cycle.

FIG. 3A shows an analytical program focussing on the state of analysis (indicated by bold solid lines) of an nth sample. Fine solid lines indicate the states of analysis of an (n+1)th sample and an (n−1)th sample, and broken lines indicate the states of analysis of an (n−2)th sample and an (n+2)th sample. FIG. 3B shows the actions of the changing valves The "metering" state a of the reaction mixture-feeding valve 47 refers to the state in which the reaction mixture can be injected into the metering tube 49 from the injection port 36, namely the state shown in FIG. 1. The "feeding" state b refers to the state in which the valve has been turned to connect the metering tube 49 to the deproteinizing column flow path The "connection" state c of the column-changing valve 52 refers to the state in which the precolumn 48 is connected to the separating column flow path. The "synchronous treatment" state d refers to the state in which the precolumn 48 is disconnected from the separating column and the transferring and cleaning solution is flown. This state d is indicated by the solid lines of 52 in FIG. 1. The action of each changing valve is repeated by each cycle.

In practising the analytical operation, the analysis of the first sample (the sample analyzed at first) is started in the first cycle. Successively, the analyses of the second sample and later samples on the autosampler are started in the second and later cycles, respectively.

FIG. 3A shows the operational program in the nth to (n+2)th cycles. It is shown that in the nth cycle, the analysis of the nth sample (the sample analyzed in the nth place) is started and the operations in the first step are conducted. This is synchronized with the previously started operations in the second step on the (n−1)th sample and with the operations in the third step on the (n−2)th sample. Next, in the (n+1)th cycle, the nth sample proceeds to the operations in the second step and the succeeding (n+1)th sample is subjected to the operations in the first step. This is synchronized with the operations in the third step on the (n−1)th sample. Further, in the (n+2)th cycle, the nth sample proceeds to the third step of operations while the (n+1)th sample undergoes the operations in the second step. Concurrently with this, the operations in the first step are conducted on the (n+2)th sample.

In the case only one sample is analyzed, the time required for the analysis with the present analyzer is the sum of the times required for the first, second and third steps, namely the total time for three cycles. However, in the case a plurality of samples are analyzed continuously, it is possible to analyze at a rate of one sample per one cycle. In the present embodiment, the analytical time required for one sample is 5 minutes because the time for one cycle is 5 minutes.

In chromatographying catecholamine derivatives, it is desired to chromatograph at least 10 samples per hour Hence, the time allowable for one cycle is 6 minutes or shorter.

Figure 4:
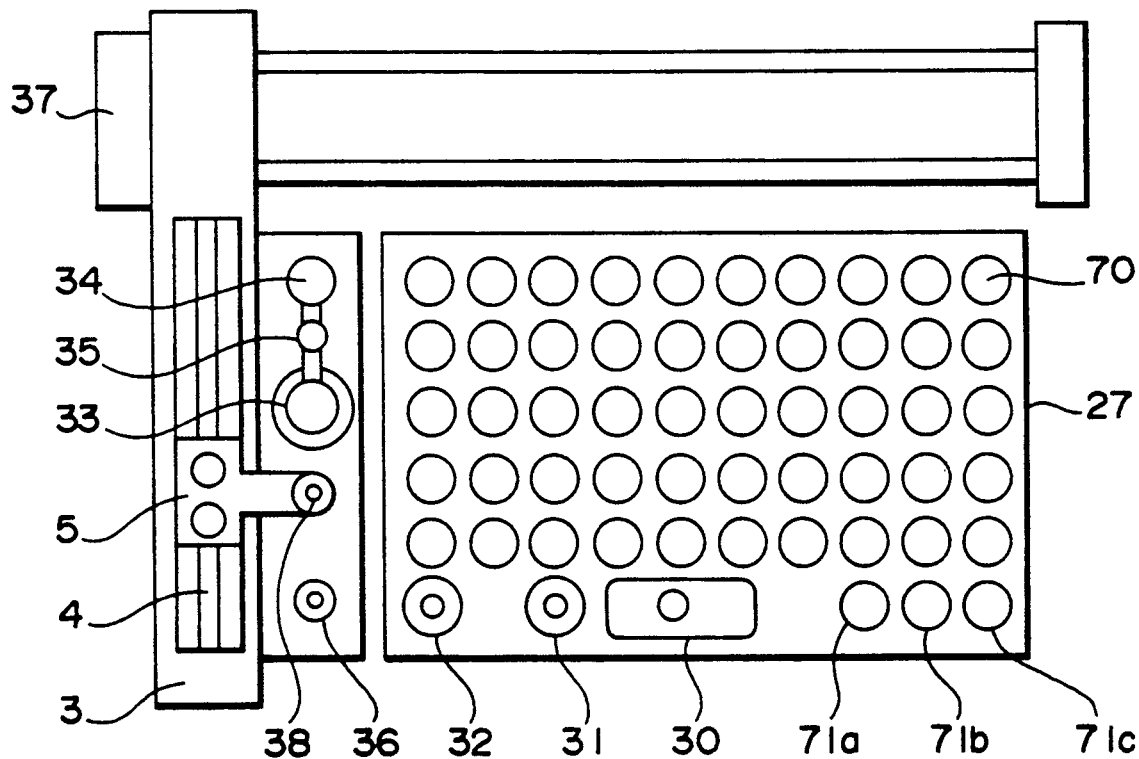
FIG. 4 is a top view of the autosampler section in the analyzer of FIG. 1.

FIG. 4 is a plan view of the autosampler 26 in the analyzer of FIG. 1. A sample rack 27 is detachably mounted on a sample stage 28. Said sample rack 27 has formed therein sample vessel-holding holes 70, arranged in ten ranks and five files (total 50 holes) in the form of a matrix. In these holes 70 are placed sample vessels each containing a sample to be analyzed. On said sample rack 27 are also provided the receptacles for a reagent 30, an internal standard solution 31 and a standard sample 32, as well as emergency sample vessel-holding holes 71a, 71b and 71c for allowing emergent cut-in measurement during analysis. On one side of said sample rack 27 are provided a reaction vessel 33, a nozzle cleaning tank 34, a drain port 35 and an injection port 36 connecting to a metering tube 49, each at the fixed position. An injection nozzle 38 is secured to a holder 5 arranged slidably on the shaft 4 of a moving block 3. Driven by a driving mechanism 37, said nozzle 38 can be moved freely in three-dimensions (the directions of X-, Y- and Z-axes) so that it is moved to the position of any of said vessels or ports for performing necessary operations.

The analytical operation is started as the operator pushes a switch for analysis start, provided on a control panel 27 after said sample rack 27 carrying the samples to be analyzed and the reagent has been set in position on the sample stage 28 of the autosampler 26.

Figure 5A:
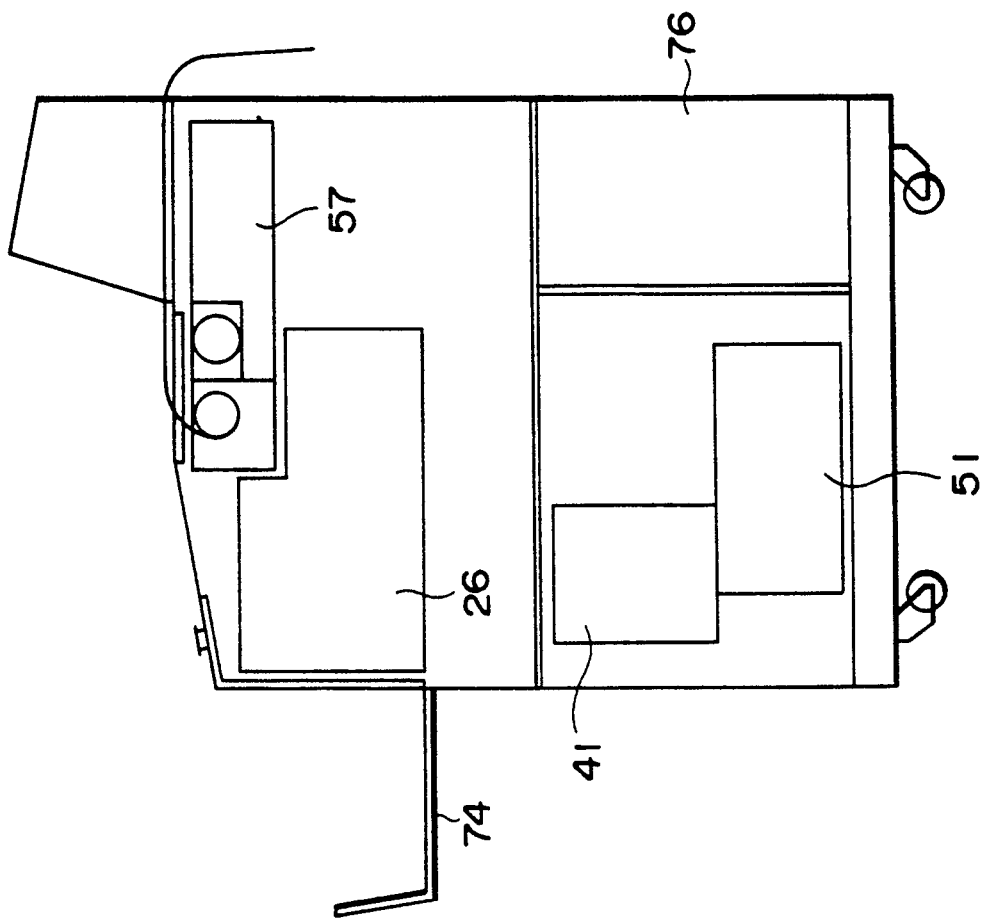
FIG. 5A is a view showing the appearance of the analyzer of FIG. 1 when viewed from the front.
Figure 5B:
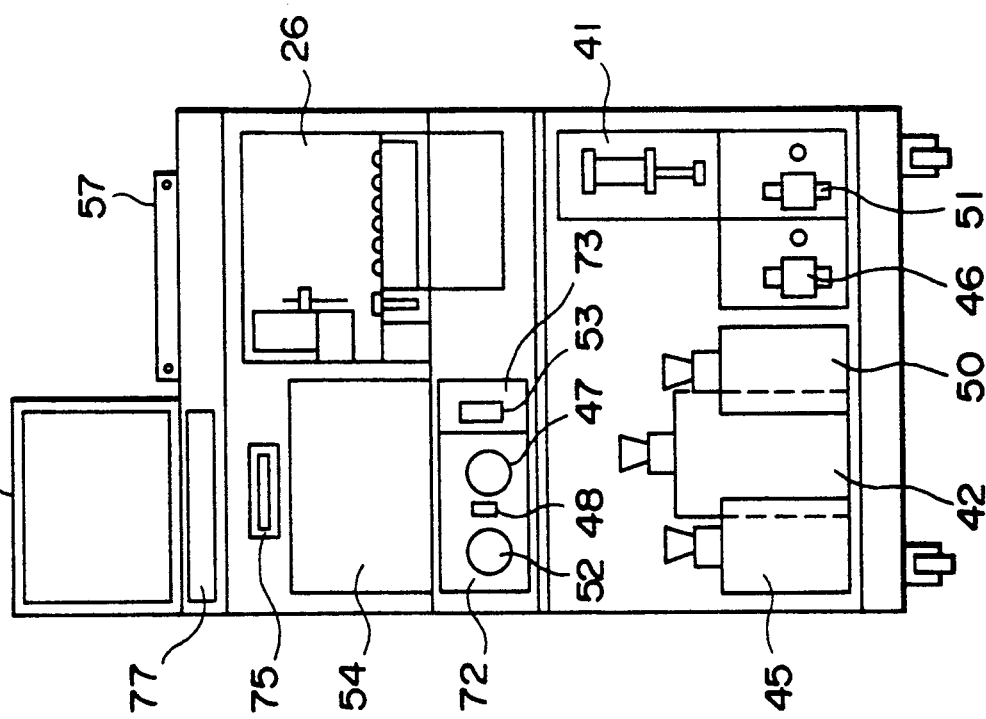
FIG. 5B is a view showing the appearance of the analyzer of FIG. 5A when viewed from the side.

FIGS. 5A and 5B show the constitution of the analyzer of FIG. 1. This catecholamine analyzer is a vertical type and has incorporated therein all the units necessary for the analysis.

The analyzer is partitioned into two stages. In the upper stage are provided an autosampler 26, a fluorophotometer 54 and a column panel 72. On the column panel 72 are provided a deproteinizing column 48, a separating column 53, a reaction mixture-feeding valve 47 and a column-changing valve 52. The separating column 53 is controlled in temperature by a thermostatic block 73 for keeping the temperature constant at a specified level during analysis. Mounting and demounting of the sample rack 27 on and from the autosampler 26 are practised by opening or closing a cover 74. A floppy disc 75 for storing data of measurements is set above the fluorophotometer 54.

In the lower stage of the analyzer are provided a cleaning solution tank 42, a transferring and cleaning solution tank 45, an eluting solution tank 50, an injection pump 41, a pump 46 for feeding the transferring and cleaning solution and a pump 51 for feeding the eluting solution. The solutions necessary for the analytical units in the upper stage of the analyzer are supplied from the lower stage. An electric unit 76 including a power source, substrates, etc. is housed in the rear portion of the lower stage of the analyzer. On the top of the analyzer are provided a printer 57, a CRT 58 and an operating panel 77 to which the information necessary for effecting the analysis by this analyzer is input.

Next, the analytical method of the present invention using the analyzer of FIG. 1 is described referring to the figure. For simplicity, there is described an example wherein substances to be analyzed are catecholamines. However, the method of the present invention is in no way restricted to this example alone.

Figure 6:
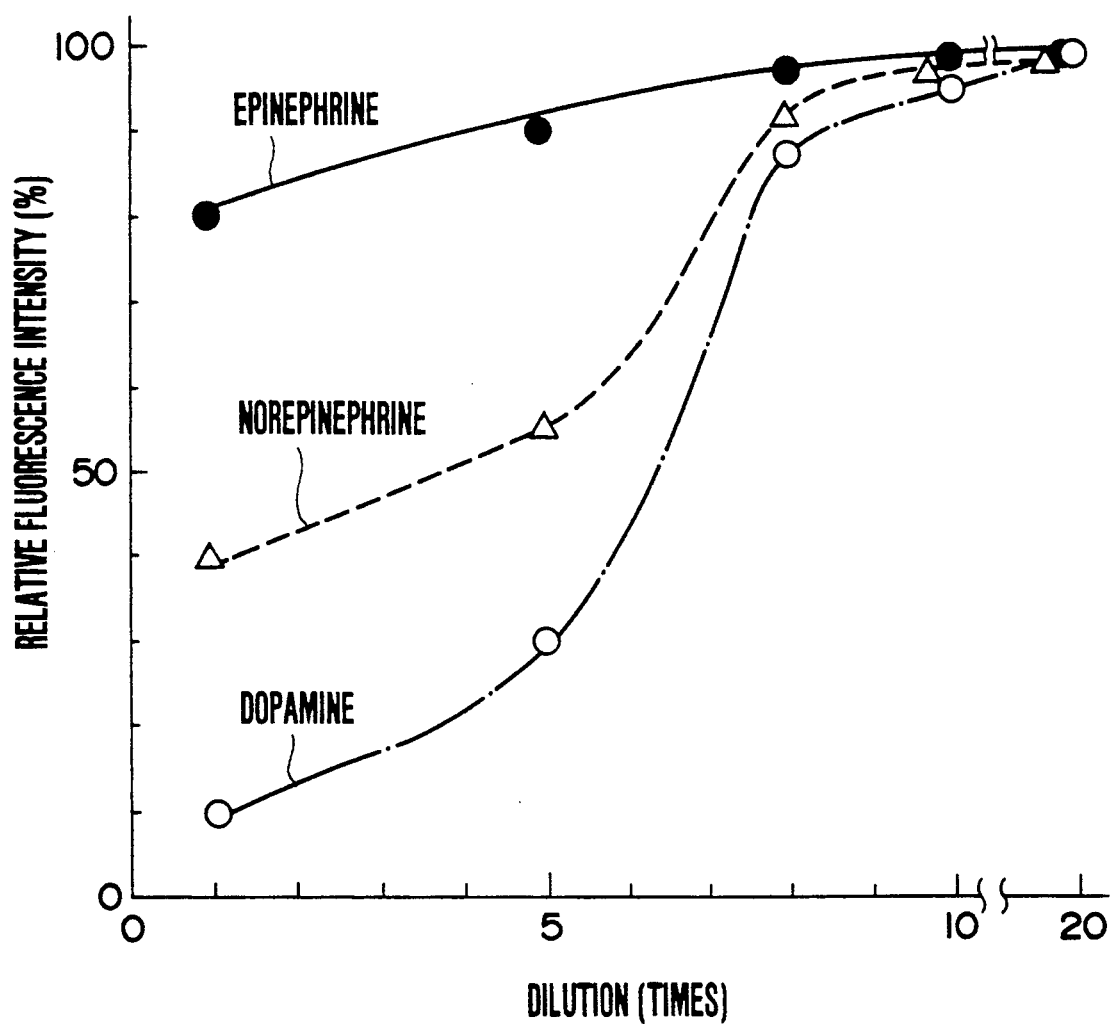
FIG. 6 is a graph showing the relationship between dilution degree (times) and relative fluorescence intensity, of a blood sample.

As the sample, a plasma or serum containing catecholamines is used. As the diluent, there can be used water, various buffer solutions and aqueous solutions containing a small amount of an organic solvent. Of these, water or a buffer solution of low concentration is preferred. The presence of a high concentration of an organic solvent in aqueous solution as a diluent may cause the denaturation, agglomeration and precipitation of the proteins contained in the sample. Shown in FIG. 6 are the dilution degree (times) used and the obtained degree of conversion of catecholamines to their derivatives, expressed in fluorescence intensity of said derivatives. The vertical axis refers to relative fluorescence intensity (the fluorescence intensities of catecholamine derivatives obtained with the sample, relative to those of catecholamine derivatives obtained with a catecholamine standard solution). Water was used as a diluent and, after the reaction for converting catecholamines to their derivatives, a deproteinizing treatment was effected using an ultrafilter membrane.

As is clear from FIG. 6, each catecholamine derivative obtained by adding a reagent directly to a sample containing catecholamines and proteins to convert the catecholamines to respective derivatives, gives a small fluorescence intensity as compared with each catecholamine derivative obtained by adding the same reagent to a standard sample containing the same amounts of the same catecholamines but no proteins. In the case of dopamine derivative, the ratio of fluorescence intensity of the former to the latter is 1:10 and this is considered to be particularly small. However, as the sample was diluted with an increasing amount of water, the fluorescence intensity of the sample increased; and when the sample was diluted 8-fold, the fluorescence intensity of the same sample increased to such a level that the presence of proteins gave substantially no adverse effect on the precision of catecholamine derivative measurement. Incidentally, the normal range of protein concentration in blood is 6.6–8.6%. As the diluent, there can be used, besides water, buffer solutions and solutions containing a salt, EDTA or a low concentration of an organic solvent. These solutions gave the same effects as water.

Now there is described an example of analysis of catecholamines in plasma, using the analyzer of FIG. 1. The analytical conditions used are shown in Table 1.

TABLE 1

| Item | Details |
|---|---|
| Separating column | Silica-ODS, 3 μm in particle diameter 4.6 mm (ID) × 60 mm |
| Deproteinizing column | Internally reversed phase packing (Chemicals Inspection and Testing Institute, Japan) 4.6 mm (ID) × 5 mm |
| Diluent | $10^{-4}$ M EDTA |
| Pretreating solution | 0.5% NaCl, $10^{-3}$ N HCl, $10^{-4}$ M EDTA |
| Eluent | $CH_3CN/CH_3OH/H_2O$ = 5/2/4 (containing 50 mM of $LiNO_3$ and 10 mM of SDS) |
| Detector | Fluorescence monitor, Ex. = 345 nm, Em. = 485 nm |
| Reagent for converting to derivatives | 10 mM 1,2-DPE, 40% $CH_3CN$, 1 mM potassium ferricyanide |

A plasma containing proteins was placed in a plurality of sample vessels 29. The sample vessels were arranged on the sample rack 27. The transferring and cleaning solution 45 and the eluting solution 50 were transferred to the deproteinizing column 48 and the separating column 53 at a rate of 1 ml/min by means of the transferring pumps 46 and 51, respectively. The eluate from the separating column 53 were monitored by the fluorophotometer 54 and, when the baseline had stabilized, the actuation of the autosampler 26 was started. The sample in the sample vessel was sucked up in an amount of 50 μl by the injection nozzle 38 and discharged into the reaction vessel 33. Further, the cleaning solution 42 was sucked up in an amount of 450 μl and discharged into the reaction vessel 33, and dilution and mixing was effected. 400 μl of the reagent 30 and 50 μl of the internal standard solution 31 were added to the contents of the reaction vessel 33, and mixing was effected by repeating suction and discharging. The mixture was allowed to stand for 3 minutes. At this time, the temperature of the reaction vessel was kept at 50° C. Thereafter, 500 μl of the reaction mixture containing the catecholamines converted to their derivatives was sucked up by the injection nozzle 38 and injected into the metering tube 49 through the injection port 36. The reaction mixture-feeding valve 47 was turned so as to allow the passage of the transferring solution 45 through the metering tube 49, and the reaction mixture containing catecholamine derivatives and proteins was passed through the deproteinizing column 48. At this time, the catecholamine derivatives in the reaction mixture were adsorbed and remained in the column 48, and the proteins were discharged from the discharge port 64. Then, the transferring and cleaning solution 45 was passed through the deproteinizing column 48 for about 3 minutes. Thereafter, the flow path-changing valve 52 was turned to allow the flow of the eluting solution 50 into the separating column 53 via the deproteinizing column 48, and concurrently therewith the printer was started.

Figure 7:
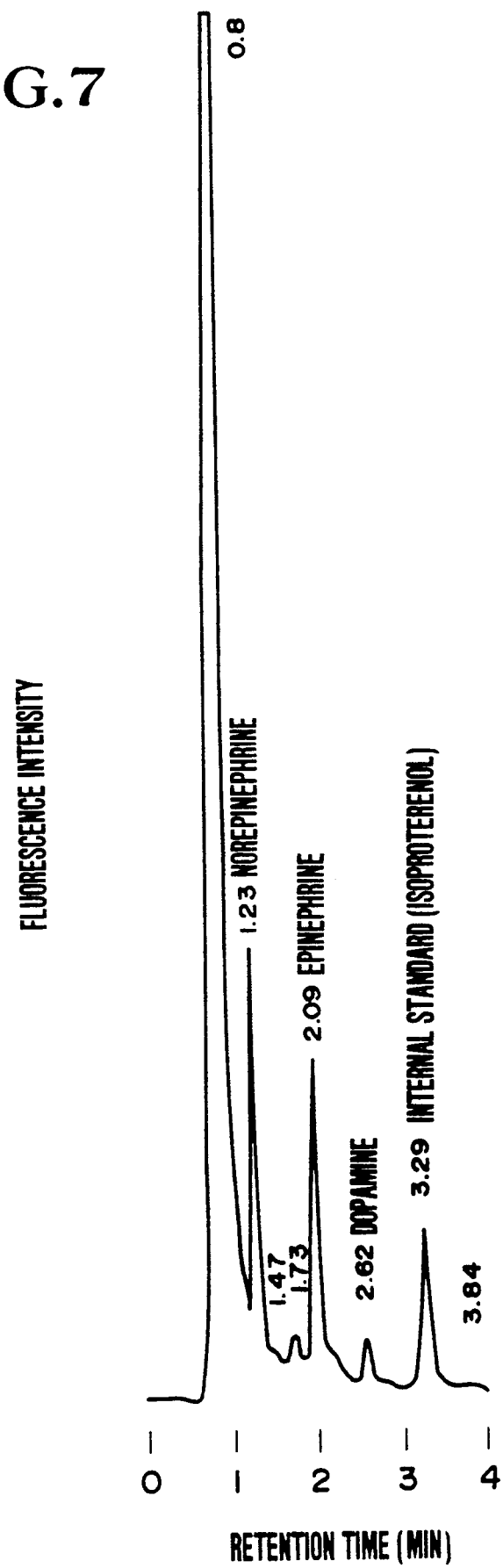
FIG. 7 is a graph showing an example of the measurement results of catecholamines when the catecholamines were analyzed by the analyzer of FIG. 1.

The thus obtained chromatogram is shown in FIG. 7. The sample used contained 50–150 pg of catecholamines and there was no practical problem in the sensitivity of analysis. The time required for separation of catecholamine derivatives into individual components was less than 4 minutes, which gave no problem in carrying out high-speed separation by synchronous treatment. The percent of proteins removed in deproteinizing column was 95% or more, which gives only a small effect on the life of separating column.

The percents of three catecholamine components and internal standard substance recovered were all 98% or more.

Figure 8:
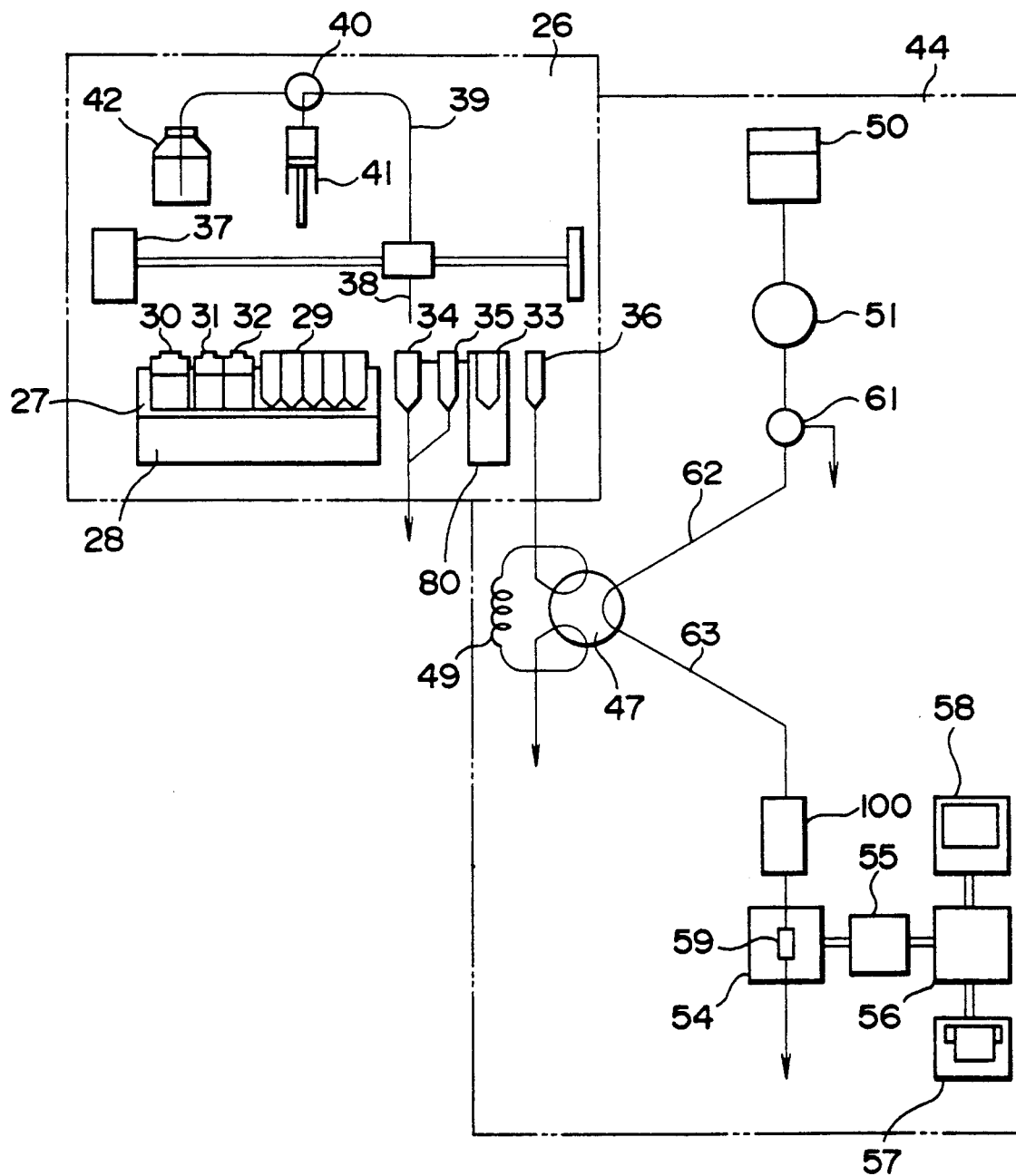
FIG. 8 is a schematic view showing the constitution of another embodiment of the analyzer of the present invention.

Another embodiment of the present analyzer is shown in FIG. 8. This embodiment differs from the embodiment of FIG. 1 in that the former has neither deproteinizing column 48 nor column-changing mechanism constituted by the flow path-changing valve 52. The units having the same functions as in the embodiment of FIG. 1 are given the same numerals as in the embodiment of FIG. 1.

In FIG. 8, a sample is subjected to a reaction for converting the physiologically active substances to their derivatives, in a diluted state in a reaction vessel 33. The reaction mixture in the reaction vessel 33 is carried to an injection port 36 by a nozzle 38 and introduced into the flow path system of an analytical section 44 by the pushing-out action of a pump 41. The reaction mixture is introduced into a separating column 100 in a predetermined amount, i.e. an amount filling a metering tube 49. In this embodiment, since no deproteinizing column is employed, the packing used in the separating column 100 is different from that used in the separating column of the analyzer of FIG. 1.

As the packing used in the separating column 100, there is selected such a packing as to allow components of very large molecular weight (e.g. proteins) to pass through the separating column 100 and as to adsorb components of smaller molecular weight (e.g. catecholamine derivatives) and of high hydrophobicity. An example of such a packing is an internally reversed phase type column such as GFF-S5-80 Packed Column marketed by Regis Chemical Company. The packing used in this column has a particle size of 5 μm, and the column has an inside diameter of 4.6 mm and a length of 15 cm. Another example of the separating column 100 is a hydrophobic polymer type column [Hisep (trade name)] marketed by Supelco. This column contains a network-protected silica-based packing having a particle size of 5 μm.

Figure 9:
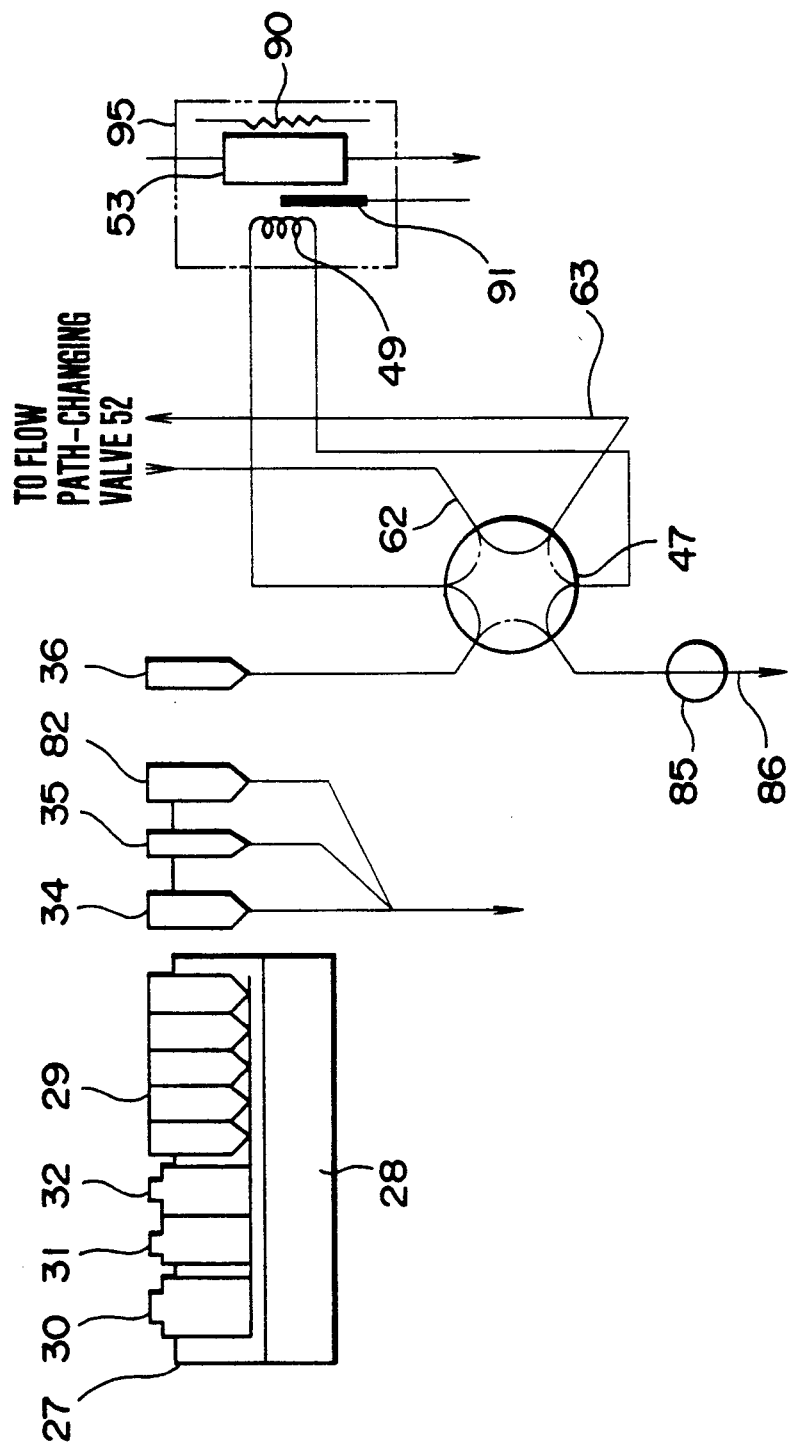
FIG. 9 is a schematic view showing the constitution of the key parts in still another embodiment of the analyzer of the present invention.

Still another embodiment of the present analyzer is shown in FIG. 9. The catecholamine analyzer of this embodiment employs basically the same flow path constitution as in the analyzer of FIG. 1; however, the flow path system of the deproteinizing column 48 and the separating column 53 is omitted in FIG. 9. In the analyzer of FIG. 9, since the operation timing of a mixture-feeding valve 47 and the suction and discharge timing of an injection nozzle 38 are different from those in the analyzer of FIG. 1, a control unit 56 controls the operations of a driving mechanism 37, an injection pump 41 and the mixture-feeding valve 47 in accordance with an operation program capable of performing operations as described below.

In the analyzer of FIG. 9, a mixing vessel 82 is used in place of the reaction vessel 33 of FIG. 1. A metering tube 49 and a separating column 53 are arranged in a thermostatic air bath 95 and are kept at 30-60° C. As necessary, the mixture-feeding valve 47 may be accommodated in the thermostatic air bath 95. In order to keep constant the inside of the bath 95 at a predetermined temperature, a heater 90 and a temperature sensor 91 are provided in the thermostatic bath 95, and the heater 90 is turned on or off in accordance with the signal of the temperature sensor 91.

In the analyzer of FIG. 9, the metering tube 49 acts as a reaction site. The solution stored in the metering tube 49 is disconnected from other flow path systems because the flow path-changing valve 47 is in a solid-line state, and is kept stagnant while an opening or closing valve 85 is put in a closed state to allow a labeling reaction (a reaction for converting the catecholamines in the sample to their derivatives) to proceed. At first, a blood sample 29 not subjected to deproteinization, a reagent 30 and a diluent 42 are transferred to the mixing vessel 82 by means of an injection nozzle 38, and mixed. Right after the conversion of cetacholamines in sample to their derivatives begins, the mixture is sucked up by the nozzle 38 and then introduced into the metering tube 49 through an injection port 36 by the action of an injection pump 41, to fill the metering tube 49 with the mixture. At this time, the mixture-feeding valve 47 is in a solid-line state; therefore, the transferring solution stored in the metering tube and the front portion of the mixture are discharged into a drain 86 via the opening or closing valve 85. Then, the valve 85 is turned to a closed state to allow the mixture to stay in the metering tube 49 and allow the reaction for converting the catecholamines contained in the sample to their derivatives, to proceed at a constant temperature in the range of 30-60° C.

After the completion of the above reaction, the mixture-feeding valve 47 is set in a solid-line state, and the reaction mixture is introduced into a deproteinizing column by a transferring solution 45 in such a way that the reaction mixture band is sandwiched between the transferring solution. The subsequent treatments are the same as in the analyzer of FIG. 1. It is not necessary to heat the mixing vessel 82 in the embodiment of FIG. 9; therefore, the analyzer can be simplified as compared with the analyzer of FIG. 1.

According to the present invention, the physiologically active substances to be analyzed, contained in a biological sample not subjected to deproteinization can be effectively converted to their derivatives without being adversely affected by the proteins also contained in the sample; accordingly, said substances in such a sample can be analyzed at a high precision. Therefore, the present invention has a large meritorious effect in practical use.

What is claimed is: PHACTS-PCS

1. A chromatographic method for analyzing a biological sample, which comprises the steps of:
    feeding a blood or cerebrospinal fluid not subject to deproteinization, a diluent and a reagent solution into a reaction vessel to effect a reaction for converting at least one physiologically active substance selected from the group consisting of catecholamines and prostaglandin to be analyzed and contained in the sample to their derivatives, thereby to obtain a reaction mixture, an amount of the diluent fed being selected such that a volume of diluent used is 8-20 times the volume of the sample,
    transferring the reaction mixture in the reaction vessel to a deproteinizing column to allow said derivatives to be adsorbed in the column and concurrently to discharge proteins also contained in the sample from the column, and
    desorbing the derivatives adsorbed in the deproteinizing column and transferring the desorbed derivatives to a separating column to separate the derivatives into individual components.

2. The method of claim 1, wherein the step of effecting a reaction for converting the at least one physiologically active substance to their derivatives includes the step of selecting a reaction temperature of 30–60° C.

3. The method of claim 1, wherein the diluent has no adverse effect on the reaction and does not cause denaturation of proteins contained in the sample.

4. The method of claim 1, wherein a plurality of samples are continuously analyzed.

5. The method of claim 1, wherein said blood or cerebrospinal fluid contains 5%–10% protein by weight.

6. The method of claim 1, wherein the diluent and the proteins are concurrently discharged from the deproteinizing column while concurrently retaining the derivatives, which are derivatized analytes of catecholamines or prostaglandins, in the deproteinizing column.

7. A chromatographic method for analyzing a biological sample, which comprises the steps of:
diluting a blood or cerebrospinal fluid not subjected to deproteinization and a reagent with a diluent, the amount of the diluent being selected such that the volume of the diluent added is 8–20 times the volume of the sample, and effecting a reaction for converting at least one physiologically active substance selected from the group consisting of catecholamines and prostaglandin to be analyzed and contained in the sample to their derivatives, thereby to obtain a reaction mixture,
transferring the reaction mixture containing the derivatives to a deproteinizing column to allow the derivatives to be adsorbed in the column and concurrently to discharge proteins also contained in the sample, from the column, and
desorbing the derivatives adsorbed in the deproteinizing column and transferring the desorbed derivatives to a separating column to separate the derivatives into individual components.

8. The method of claim 7, wherein the step of effecting a reaction for converting the at least one physiologically active substance to their derivatives includes the step of selecting prostaglandin as the at least one physiologically active substance and selecting monodansylcadaverine as the reagent.

9. The method of claim 7, wherein said blood or cerebrospinal fluid contains 5%–10% protein by weight.

10. The method of claim 7, wherein the diluent and the proteins are concurrently discharged from the deproteinizing column while concurrently retaining the derivatives, which are derivatized analytes of the catecholamines and prostaglandin, in the deproteinizing column.

11. The method of claim 7, wherein the diluent has no adverse effect on the reaction and does not cause denaturation of proteins contained in the sample.

12. The method of claim 7, wherein a concentration of protein in a resulting mixture of the sample, the reagent and the diluent is at most 1% by weight.

13. A chromatographic method for analyzing a biological sample, which comprises the steps of:
feeding a blood or cerebrospinal fluid not subjected to deproteinization, a diluent of 8–20 times the volume of the sample and a reagent into a vessel to prepare a mixture,
transferring the mixture to a reaction flow path and stopping the liquid movement in the path for a predetermined length of time to effect a reaction for converting at least one physiologically active substance selected from the group consisting of catecholamines and prostaglandin to be analyzed and contained in the sample to their derivatives, thereby to obtain a reaction mixture, and
transferring the reaction mixture containing the derivatives to a separating column packed with an internally reversed phase type packing or a network-protected silica-based packing to separate the derivatives into individual components.

14. The method of claim 13, wherein the reaction mixture containing the derivatives is transferred to the separating column without being subjected to a deproteinization treatment.

15. The method of claim 14, wherein the separating column is packed with a packing on which proteins cause substantially no damage.

16. The method of claim 13, wherein said blood or cerebrospinal fluid contains 5%–10% protein by weight.

17. The method of claim 13, wherein the diluent has no adverse effect on the reaction and does not cause denaturation of proteins contained in the sample.

18. A chromatographic method for analyzing a biological sample, which comprises the steps of:
mixing a biological sample not subjected to deproteinization, a reagent and a diluent to dilute the sample, the amount of the diluent added being 8–20 times the volume of the sample, and effecting a reaction for converting at least one physiologically active substance selected from the group consisting of catecholamines and prostaglandin to be analyzed and contained in the sample to their derivatives, thereby to obtain a reaction mixture, and
transferring the reaction mixture containing the derivatives to a separating column packed with an internally reversed phase type packing or a network-protected silica-based packing, to separate the derivatives into individual components.

19. The method of claim 18, wherein the reaction mixture containing the derivatives is transferred to the separating column without being subjected to a deproteinization treatment.

20. The method of claim 18, wherein said blood or cerebrospinal fluid contains 5%–10% protein by weight.

21. The method of claim 18, wherein the diluent has no adverse effect on the reaction and does not cause denaturation of proteins contained in the sample.

22. The method of claim 18, wherein a concentration of protein in a resulting mixture of the sample, the reagent and the diluent is at most 1% by weight.

23. A chromatographic method for analyzing a biological sample, which comprises the steps of:
diluting a blood or cerebrospinal fluid not subjected to deproteinization and a reagent with a diluent, the amount of the diluent being selected so as to be 8–20 times the volume of the sample, and effecting a reaction for converting the physiologically active substances to be analyzed and contained in the sample to their derivatives, thereby to obtain a reaction mixture, wherein the step of effecting a reaction for converting the physiologically active substances to their derivatives includes the step of selecting catecholamines as the physiologically active substances and selecting 1,2-diphenylethylene-diamine as the reagent, transferring the reaction mixture containing the derivatives to the deproteinizing column to allow the derivatives to be adsorbed in the column and concurrently to discharge proteins also contained in the sample, from the column, and desorbing the derivatives adsorbed in the deproteinizing column and transferring the desorbed derivatives to a separating column to separate the derivatives into individual components.

24. The method of claim 23, wherein the diluent and the proteins are concurrently discharged from the deproteinizing column while concurrently retaining the derivatives, which are derivatized analytes of catecholamines, in the deproteinizing column.

25. The method of claim 23, wherein the diluent has no adverse effect on the reaction and does not cause denaturation of proteins contained in the sample.

26. The method of claim 23, wherein a concentration of protein in a resulting mixture of the sample, the reagent and the diluent is at most 1% by weight.

27. A chromatographic method for analyzing a biological sample, which comprises the steps of:

feeding a sample of blood or cerebrospinal fluid containing catecholamines and not subjected to deproteinization, a diluent of 8-20 times the volume of the sample and 1,2-diphenylethylenediamine as a reagent into a vessel to prepare a mixture.

transferring the mixture to a reaction flow path and stopping the liquid movement in the path for a predetermined length of time to effect a reaction for converting physiologically active substances to be analyzed and contained in the sample to their derivatives, thereby to obtain a reaction mixture, and transferring the reaction mixture containing the derivatives to a separating column packed with an internally reversed phase type packing or a network-protected silica-based packing to separate the derivatives into individual components.

28. The method of claim 27, wherein the diluent has no adverse effect on the reaction and does not cause denaturation of proteins contained in the sample.

29. A chromatographic method for analyzing a biological sample, which comprises the steps of:

feeding the biological sample, containing blood or cerebrospinal fluid not subjected to deproteinization, a diluent and a reagent solution into a reaction vessel to effect a reaction for converting at least one of catecholamines and prostaglandins of the blood or cerebrospinal fluid to be analyzed and contained in the sample to their derivatives, which derivatives can be separated into individual components in a separating column, the at least one of catecholamines and prostaglandins being substances which can be converted to derivatives which can be separated in said separating column, an amount of the diluent fed being selected so as to be 8-20 times an amount of the biological sample; and transferring the derivatives to a separating column to separate the derivatives into the individual components.

30. The method of claim 29, wherein said diluent is fed such that a protein concentration in a mixture of the biological sample, the diluent and the reagent solution is at most 1% by weight.

31. The method of claim 29, wherein the diluent has no adverse effect on the reaction and does not cause denaturation of proteins contained in the sample.

32. A chromatographic method for analyzing a sample containing at least one of catecholamines and prostaglandins, and also containing protein, which comprises the steps of:

feeding the sample, not having been subjected to deproteinization, a diluent and a reagent solution so as to mix the sample, the diluent and the reagent solution in order to form a resulting mixture, an amount of diluent being selected so as to be 8-20 times a volume of the sample, and effecting a reaction to convert the at least one of catecholamines and prostaglandins to be analyzed, to their derivatives; and transferring the derivatives to a separating column to separate the derivatives into individual components.

33. The method of claim 32, wherein a concentration of protein in the resulting mixture is at most 1% by weight.

34. The method of claim 32, wherein a reaction mixture is formed upon effecting the reaction, and wherein the method includes the further step, subsequent to said effecting a reaction and prior to said transferring the derivatives to the separating column, of transferring the reaction mixture containing the derivatives to a deproteinizing column to allow the derivatives to be adsorbed in the deproteinizing column and concurrently to discharge the proteins from the deproteinizing column.

35. The method of claim 34, wherein the diluent and the proteins are concurrently discharged from the deproteinizing column, while concurrently retaining the derivatives, which are derivatized analytes of the at least one of catecholamines and prostaglandins, in the deproteinizing column.

36. A chromatographic method for analyzing a biological sample, which comprises the steps of:

feeding a blood or cerebrospinal fluid not subject to deproteinization, a diluent and a reagent solution into a reaction vessel to effect a reaction for converting at least one physiologically active substance selected from the group consisting of catecholamines and prostaglandin to be analyzed and contained in the sample to their derivatives, thereby to obtain a reaction mixture, the diluent having no adverse effect on the reaction and not causing denaturation of proteins contained in the sample, the diluent being selected from the group consisting of water, an aqueous neutral salt solution and a buffer solution, transferring the reaction mixture in the reaction vessel to a deproteinizing column to allow said derivatives to be adsorbed in the column and concurrently to discharge the proteins also contained in the sample from the column, and desorbing the derivatives adsorbed in the deproteinizing column and transferring the desorbed derivatives to a separating column to separate the derivatives into individual components.

37. A chromatographic method for analyzing a biological sample, which comprises the steps of:

feeding a blood or cerebrospinal fluid not subject to deproteinization, a diluent and a reagent solution into a reaction vessel to effect a reaction for converting at least one physiologically active substance selected from the group consisting of catecholamines and prostaglandin to be analyzed and contained in the sample to their derivatives, thereby to obtain a reaction mixture, the diluent having no adverse effect on the reaction and not causing denaturation of proteins contained in the sample, the diluent being ethylenediaminetetraacetic acid, transferring the reaction mixture in the reaction vessel to a deproteinizing column to allow said derivatives to be adsorbed in the column and concurrently to discharge the proteins also contained in the sample from the column, and desorbing the derivatives adsorbed in the deproteinizing column and transferring the desorbed derivatives to a separating column to separate the derivatives into individual components.

* * * * *